(12) United States Patent
Kim et al.

(10) Patent No.: US 11,691,934 B2
(45) Date of Patent: Jul. 4, 2023

(54) SYNTHESIS METHOD AND SYNTHESIS DEVICE FOR CYCLODODECENE

(71) Applicant: HANWHA SOLUTIONS CORPORATION, Seoul (KR)

(72) Inventors: Youngjin Kim, Daejeon (KR); Namjin Jang, Daejeon (KR); Kyuho Song, Daejeon (KR); Wook Jeong, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 0 days.

(21) Appl. No.: 17/413,566

(22) PCT Filed: Oct. 4, 2019

(86) PCT No.: PCT/KR2019/013029
§ 371 (c)(1),
(2) Date: Jun. 13, 2021

(87) PCT Pub. No.: WO2020/130304
PCT Pub. Date: Jun. 25, 2020

(65) Prior Publication Data
US 2022/0055970 A1    Feb. 24, 2022

(30) Foreign Application Priority Data

Dec. 19, 2018  (KR) .................. 10-2018-0165183

(51) Int. Cl.
*C07C 5/05* (2006.01)
*B01F 27/81* (2022.01)
(Continued)

(52) U.S. Cl.
CPC ............ *C07C 5/05* (2013.01); *B01F 23/2331* (2022.01); *B01F 27/112* (2022.01); *B01F 27/81* (2022.01);
(Continued)

(58) Field of Classification Search
CPC ... C07C 5/05; C07C 2531/02; C07C 2531/30; C07C 2601/20; C07C 2527/13;
(Continued)

(56) References Cited

U.S. PATENT DOCUMENTS 3,400,164 A     9/1968 Mcalister
6,194,624 B1 *  2/2001 Pinkos ...................... C07C 5/05
                                                         585/277
(Continued)

FOREIGN PATENT DOCUMENTS

JP     2000169402 A    6/2000
JP     2002030006      1/2002
(Continued)

OTHER PUBLICATIONS

International Search Report dated Jan. 14, 2020.
JP Office Action dated Sep. 12, 2022.

*Primary Examiner* — In Suk C Bullock
*Assistant Examiner* — Jason Y Chong
(74) *Attorney, Agent, or Firm* — Harvest IP Law, LLP (57) ABSTRACT

A synthesis method and a synthesis device of cyclododecene according to the present invention have a high conversion rate of cyclododecatriene which is a reactant and a high selectivity of cyclododecene which is a required product, and even so, have an effect of significantly decreasing a reaction time. In addition, the method and the device have an excellent conversion rate of cyclododecatriene and an excellent selectivity of cyclododecene, while maintaining excellent reactivity without an organic solvent such as ethanol. Therefore, a volume of the reactor relative to an output of cyclododecene may be further decreased. Moreover, the method and the device may minimize costs for facilities and (Continued)

process, are practical, decrease a process time, and are industrially advantageous for mass production as compared with the conventional art.

9 Claims, 3 Drawing Sheets

(51) Int. Cl.
| | | |
|---|---|---|
| *B01F 23/233* | (2022.01) | |
| *B01F 35/221* | (2022.01) | |
| *B01F 27/112* | (2022.01) | |
| *B01J 8/02* | (2006.01) | |
| *B01J 27/13* | (2006.01) | |
| *B01J 31/02* | (2006.01) | |
| *B01F 101/00* | (2022.01) | |

(52) U.S. Cl.
CPC ............ *B01F 35/2214* (2022.01); *B01J 8/02* (2013.01); *B01J 27/13* (2013.01); *B01J 31/0207* (2013.01); *B01J 31/0267* (2013.01); *B01F 23/23314* (2022.01); *B01F 2101/2204* (2022.01); *B01J 2208/00867* (2013.01); *B01J 2231/645* (2013.01); *C07C 2531/02* (2013.01); *C07C 2531/30* (2013.01)

(58) Field of Classification Search
CPC ............... C07C 13/275; B01F 23/2331; B01F 23/23314; B01F 27/112; B01F 27/81; B01F 35/2214; B01F 2101/2204; B01J 8/02; B01J 8/10; B01J 27/13; B01J 31/0207; B01J 31/0267; B01J 31/2208; B01J 31/2404; B01J 2208/00787; B01J 2208/00858; B01J 2208/00867; B01J 2208/00902; B01J 2208/00911; B01J 2231/645; B01J 2531/821; B01J 4/007; B01J 19/0066; B01J 19/18; B01J 2219/00051; B01J 2219/00189
See application file for complete search history.

(56) References Cited

U.S. PATENT DOCUMENTS

| | | | | |
|---|---|---|---|---|
| 2008/0275276 A1* | 11/2008 | Teles | ............... | C07C 45/28 |
| | | | | 568/363 |
| 2018/0346398 A1* | 12/2018 | Liao | ............... | C07C 29/20 |

FOREIGN PATENT DOCUMENTS

| | | |
|---|---|---|
| JP | 2007506694 | 3/2007 |
| JP | 4523301 B2 | 8/2010 |
| KR | 1020060050500 | 5/2006 |

\* cited by examiner

SYNTHESIS METHOD AND SYNTHESIS DEVICE FOR CYCLODODECENE

CROSS-REFERENCE TO RELATED APPLICATIONS

This application is a National Stage of International Application No. PCT/KR2019/013029 filed Oct. 4, 2019, claiming priority based on Korean Patent Application No. 10-2018-0165183 filed Dec. 19, 2018.

TECHNICAL FIELD

The present invention relates to a synthesis method and a synthesis device of cyclododecene having a higher conversion rate of reactants and a higher selectivity of cyclododecene.

BACKGROUND ART

Synthesis of cyclododecene (ODEN) by a selective hydrogenation reaction using cyclododecatriene (CDT) as a starting material is often described in the literatures, and many studies for improving the yield of cyclododecene have been conducted.

For example, cyclododecatriene including trans-1,5,9-cyclododecatriene produces by-products such as cyclododecadiene (CDDN) and cyclododecan (CDAN) in addition to cyclododecene, in a hydrogenation reaction and the by-products remain until the end of the reaction, thereby decreasing the conversion rate of cyclododecatriene and the selectivity of cyclododecene.

In order to synthesize cyclododecene in a high conversion rate (yield), U.S. Pat. No. 5,180,870 A discloses a technology for a homogeneous catalyst by a RU complex of cyclododecatriene and hydrogenation by an amine compound. However, in this technology, it is difficult to separate a catalyst and an amine compound from cyclododecatriene, and there is a possibility that the product cyclododecene is polluted with an amine.

In the preparation of cyclododecene by a metal oxide catalyst, hydrogenation by mass transfer of gas/liquid/solid in a liquid phase by a heterogeneous catalyst, continuous three-stage hydrogenation in a fixed bed, continuous gaseous hydrogenation, and the like are possible.

Though the synthesis method of cyclododecene for improving a conversion rate has been variously studied, there is still no specific and substantial means for a method and a device for utilizing this in large scale industrial and commercial environments, which is currently unsatisfactory.

Specifically, in order to industrially use cyclododecene, it should be synthesized in large quantities, and process efficiency of facilities, maintenance, repair, and the like of the device therefor should be high. As an example, Japanese Patent Registration Publication No. (JP) 4523301 B2 discloses a synthesis method of cyclododecene using selective heterogeneous hydrogenation using cyclododecatriene as a starting material, which may be realized in an industrial scale and uses an easily usable catalyst. However, the patent uses a common fixed bed reactor for realizing an industrial scale, and thus, there is limitation in the selectivity of about 62-90% which is significantly low.

More specifically, from the view point of reactants and the reaction thereof, when a conventionally known common means for increasing a contact area of cyclododecatriene and hydrogen for increasing the conversion rate is adopted, complete hydrogenation of cyclododecatriene proceeds, so that the selectivity to cyclododecene which is a required product is decreased.

In addition, conventionally, it was required to control the use content of an organic solvent and the like for increasing the conversion rate of the reactants and the selectivity of the required product, reproducibility was deteriorated, and in particular, a time to satisfy the required conversion rate, that is, a reaction time relative to an output of the required product became very long. Therefore, massification and commercialization of the synthesis of cyclododecene were very difficult with the conventional technology.

Accordingly, a study for a synthesis method of cyclododecene in which a reaction time is significantly decreased so that mass production is industrially easily performed while having excellent conversion rate of cyclododecatriene and selectivity of the synthesized cyclododecene, and a synthesis device therefor is needed.

DISCLOSURE

Technical Problem

An object of the present invention is to provide a synthesis method and a synthesis device of cyclododecene, in which the selectivity of cyclododecene which is a required product is high while the conversion rate of cyclododecatriene which is a reactant is high, but a reaction time is significantly decreased.

Another object of the present invention is to provide a synthesis method and a synthesis device of cyclododecene, in which the conversion rate of cyclododecatriene and the selectivity of cyclododecene are excellent while excellent reactivity is maintained without an organic solvent such as acetic acid or ethanol.

Another object of the present invention is to provide a synthesis method and a synthesis device of cyclododecene, in which the volume of a reactor relative to a produced amount of cyclododecene may be further decreased while excellent reactivity is maintained without an organic solvent.

Still another object of the present invention is to provide a synthesis method and a synthesis device of cyclododecene, which may minimize costs of facilities and process, is practical, has a decreased process time, and is industrially advantageous for mass production as compared with the conventional art.

Technical Solution

The synthesis method of cyclododecene according to the present invention includes a hydrogenation step of subjecting cyclododecatriene to a partial hydrogenation reaction under a catalyst to synthesize cyclododecene, wherein in the hydrogenation, cyclododecatriene and a hydrogen gas are reacted in a stirring tank reactor provided with a gas induction hollow-type agitator to synthesize cyclododecene.

In the hydrogenation, the reaction may be carried out by stirring the gas induction hollow-type agitator, and the hydrogen gas may be supplied to cyclododecatriene through a hollow portion of the gas induction hollow-type agitator.

In an exemplary embodiment of the present invention, the stirring tank reactor may include a reaction space formed inside, and the reaction space may include a gaseous space formed in an upper portion and having a hydrogen gas and a liquid space formed in a lower portion and having a mixture including cyclododecatriene and the catalyst.

In an exemplary embodiment of the present invention, the gas induction hollow-type agitator may include an impeller shaft having a hollow portion inside to have openings formed in each of a one end portion and the other end portion; and an impeller formed in the one end portion of the impeller shaft, in which the opening is formed to communicate with an outside of the agitator, wherein in the hydrogenation, stirring may be performed while the opening formed in the one end portion of the impeller shaft where the impeller is positioned is positioned in the liquid space, and the opening formed in the other end portion of the impeller shaft is positioned in the gaseous space.

In an exemplary embodiment of the present invention, in the hydrogenation, a stirring speed may be 400 to 3,000 rpm.

In an exemplary embodiment of the present invention, in the hydrogenation, a reaction pressure may be 10 to 80 bar.

In an exemplary embodiment of the present invention, in the hydrogenation, a reaction temperature may be 100 to 200° C.

In an exemplary embodiment of the present invention, the catalyst may include a homogeneous catalyst, and the homogeneous catalyst may include ruthenium chloride, triphenylphosphine, and formaldehyde.

In an exemplary embodiment of the present invention, a mole ratio of the ruthenium chloride and the triphenylphosphine may be 1:100 to 300, and a mole ratio of the triphenylphosphine and the formaldehyde may be 1:1 to 2.

The cyclododecene synthesized by the synthesis method of cyclododecene according to an exemplary embodiment of the present invention may be used for laurolactam synthesis.

A reactor for synthesizing cyclododecene according to the present invention is to subject cyclododecatriene to a partial hydrogenation reaction under a catalyst to synthesize cyclododecene, the reactor including: a reaction unit having a reaction space formed inside; and a gas induction hollow-type agitator provided in the reaction space, wherein the gas induction hollow-type agitator includes an impeller shaft having a hollow portion inside to have openings formed in each of a one end portion and the other end portion; and an impeller formed in the one end portion of the impeller shaft, in which the opening is formed to communicate with an outside of the agitator.

In the reactor for synthesizing cyclododecene according to the present invention, the reaction space may include a gaseous space formed in an upper portion and having a hydrogen gas; and a liquid space formed in a lower portion and having a mixture including cyclododecatriene and the catalyst, and the opening formed in the one end portion of the impeller shaft where the impeller is positioned may be positioned in the liquid space and the opening formed in the other end portion of the impeller shaft may be positioned in the gaseous space.

Advantageous Effects

The synthesis method and the synthesis device of cyclododecene according to the present invention have a high conversion rate of cyclododecatriene which is a reactant and also a high selectivity of cyclododecene which is a required product, and even so, have an effect of significantly decreasing a reaction time.

The synthesis method and the synthesis device of cyclododecene according to the present invention have an effect of an excellent conversion rate of cyclododecatriene and an excellent selectivity of cyclododecene while maintaining excellent reactivity without an organic solvent.

The synthesis method and the synthesis device of cyclododecene according to the present invention have an effect of further decreasing a volume of a reactor relative to an output of cyclododecene while maintaining excellent reactivity without an organic solvent.

The synthesis method and the synthesis device of cyclododecene according to the present invention may minimize costs for facilities and process, is practical, decreases a process time, and is industrially advantageous for mass production as compared with the conventional art.

The effects described in the specification which are expected by the technical features of the present invention and the intrinsic effects are regarded as being described in the specification of the present invention, though the effects are not explicitly mentioned in the present invention.

BEST MODE

Hereinafter, the synthesis method and the synthesis device of cyclododecene according to the present invention will be described in detail with reference to accompanying drawings.

The drawings illustrated in the present specification are provided by way of example so that the idea of the present invention may be sufficiently conveyed to a person skilled in the art. Therefore, the present invention is not limited to the provided drawings, but may be embodied in many different forms, and the drawings may be exaggerated in order to clear the spirit of the present invention.

Technical terms and scientific terms used in the present specification have the general meaning understood by those skilled in the art to which the present invention pertains unless otherwise defined, and a description for the known function and configuration obscuring the gist of the present invention will be omitted in the following description and the accompanying drawings.

The singular form of the term used herein may be intended to also include a plural form, unless otherwise indicated.

The terms referring each step such as s1, s2, s3, . . . ; a1, a2, a3, . . . ; b1, b2, b3, . . . ; and a, b, c, . . . mentioned in the present specification themselves are only used for indicating any step, means, or the like, and are not construed as meaning an order relation of each object referred to by the terms.

The unit of % used herein without particular mention refers to % by weight, unless otherwise defined.

In a process of subjecting cyclododecatriene to a partial hydrogenation reaction to synthesize cyclododecene, the present inventors made an intensive effort to significantly decrease a reaction time while having a high conversion rate of a reactant and a high selectivity of a required product, and as a result, found that when a means using a gas induction hollow-type agitator is adopted to proceed with the reaction, excellent reactivity is maintained without an organic solvent used for increasing the characteristics and also a reaction time is significantly decreased while having the high characteristics.

In addition, conventionally, when a hydrogen gas is reacted with a reactant having a multiple bond, in the case in which a contact area of the reactant and the hydrogen gas is too large, a hydrogenation reaction proceeds to the end, thereby producing cyclododecane (CDAN) having no double bond to decrease a selectivity to cyclododecene having a double bond, and thus, it is difficult to control this for solving the problem. For example, in the conventional synthesis technology of cyclododecene by a partial hydrogenation reaction of cyclododecatriene, it was very difficult to select a substantial means and a device for real massification and commercialization as to the degree to which mixing and dispersion of a liquid phase including cyclododecatriene and a gaseous phase including a hydrogen gas should be performed, what should be adopted as the means for performing it, how it should be controlled, and the like, and to perform specific implementation therefor.

However, in the present invention, when a gas induction hollow-type agitator is used in a process of synthesizing cyclododecene by a partial hydrogenation reaction of cyclododecatriene, a contact area of cyclododecatriene and a hydrogen gas is greatly increased to improve a conversion rate of a reactant, but a decrease in a selectivity to cyclododecene due to an increase in the contact area is not substantially shown. Besides, a high level of conversion rate and selectivity is implemented without use of an organic solvent and the like.

Hereinafter, the synthesis method and the synthesis device of cyclododecene according to the present invention will be described in detail.

The synthesis method of cyclododecene according to the present invention includes a hydrogenation step of subjecting cyclododecatriene to a partial hydrogenation reaction under a catalyst to synthesize cyclododecene, wherein in the hydrogenation, cyclododecatriene and a hydrogen gas are reacted in a stirring tank reactor provided with a gas induction hollow-type the agitator 200 to synthesize cyclododecene.

Specifically, in the hydrogenation, the reaction is carried out by rotating/stirring the gas induction hollow-type agitator 200, and the hydrogen gas is supplied to cyclododecatriene through a hollow portion 213 of the gas induction hollow-type agitator 200. Since the gas induction hollow-type agitator 200 has a passage of the hollow portion 213 inside, the hydrogen gas flows in through the passage of the hollow portion 213 and is brought into contact with cyclododecatriene, so that a partial hydrogenation reaction proceeds. Here, the gas induction hollow-type agitator 200 rotates around a shaft 210 to apply a negative pressure to an inside of the hollow portion 213, so that the hydrogen gas is supplied to cyclododecatriene. Even in the case in which an internal pressure of the stirring tank reactor is maintained constant, a pressure difference occurs in the contact portion in a series of processes of bringing the hydrogen gas into contact with cyclododecatriene through the hollow portion 213 of the gas induction hollow-type agitator 200 and at the moment of contact and reaction, and the contact area of cyclododecatriene and the hydrogen gas becomes partially different per each unit area.

That is, as the shaft 210 where an impeller 220 is positioned is more distant from the center of the shaft, the contact area of cyclododecatriene and the hydrogen gas is gradually decreased. As the partial hydrogenation reaction of cyclododecatriene proceeds in the state that a difference in the contact area partially occurs as such, an effect of dramatically decreasing a reaction time while having a high conversion rate of the reactant and a high selectivity to cyclododecene is implemented. Besides, excellent reactivity is maintained without use of an organic solvent and the effects are implemented.

The stirring tank reactor includes a reaction unit 100 including an inner space in which cyclododecatriene and the hydrogen gas may stay and is provided with a gas induction hollow-type agitator 200 in the inner space, and anything is fine as long as it has a structure in which an agitator 200 is provided in the inner space of the reactor so that the hydrogen gas is brought into contact with cyclododecatriene through the hollow portion 213 of the gas induction hollow-type agitator 200.

Figure 1:
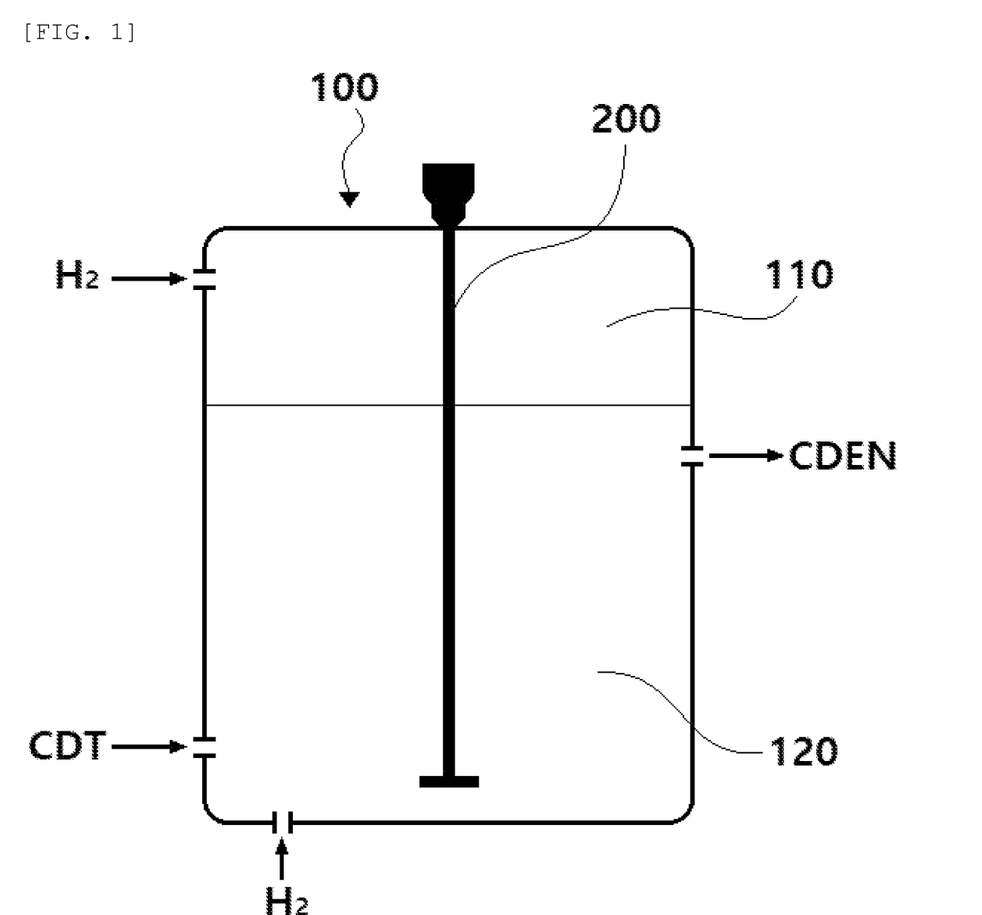
FIG. 1 is a process diagram schematically illustrating a synthesis method of cyclododecene according to the present invention.

The stirring tank reactor will be described in detail. As shown in FIG. 1, the stirring tank reactor may include the reaction unit 100 having a reaction space formed inside. The reaction space may include the gaseous space 110 formed in the upper portion and having a hydrogen gas; and a liquid space 120 formed in the lower portion and having a mixture including cyclododecatriene and a catalyst. Here, a gas induction hollow-type agitator 200 is only provided in the inner space of the reactor so that the hydrogen gas may be brought into contact with cyclododecatriene through the hollow portion 213 of the agitator 200.

Since other specific structures of the stirring tank reactor which has not been mentioned, for example, a space size, a space shape, a reactor specification/scale, and the like may be appropriately adjusted without being limited, any known literature may be referenced.

Figure 2:
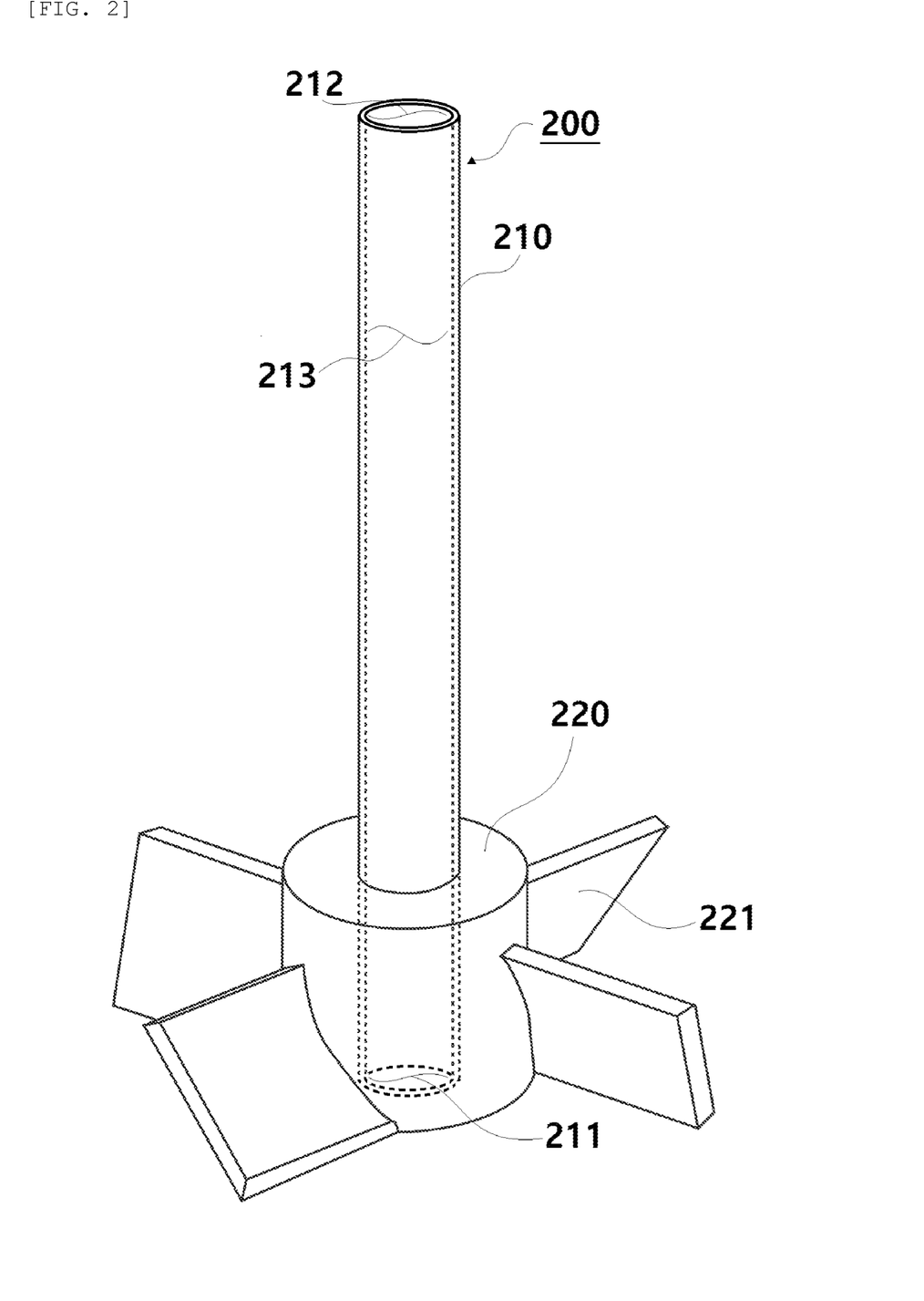
FIGS. 2 and 3 are drawings illustrating an example of a gas induction hollow-type agitator according to the present invention.

The gas induction hollow-type agitator 200 will be described in detail. As shown in FIG. 2, the gas induction hollow-type agitator 200 may include the impeller shaft 210 having the hollow portion 213 inside to have openings formed in each of a one end portion and the other end portion; and the impeller 220 formed in the one end portion of the impeller shaft 210, in which the opening is formed to communicate with an outside of the agitator 200.

For the structure provided with the gas induction hollow-type agitator 200, any structure in which an opening 211 formed in a one end portion of the impeller shaft 210 where the impeller 220 is positioned is positioned in the liquid space 120 so that the hydrogen gas is brought into contact with cyclododecatriene through the hollow portion 213 of the agitator 200, an opening 212 formed in the other end portion of the impeller shaft 210 is positioned in the gaseous space 110, and stirring may be performed in the hydrogenation. That is, the opening 211 formed in the one end portion of the impeller shaft 210 and the opening 212 formed in the other end portion of the impeller shaft 210 communicate with each other through the hollow portion 213, so that the hydrogen gas is supplied.

The structure to which the hydrogen gas is supplied is not limited as long as the hydrogen gas may be supplied to the inner space of the reactor, and in the structure, the hydrogen gas may be supplied to the gaseous space 110, the liquid space 120, or both of them, and there may be a supplying inlet in the inside of the reactor in which the hydrogen gas may be supplied to each space. As a specific example, as shown in FIG. 1, an opening formed in the one end portion of the impeller shaft 210 where the impeller 220 is positioned may be provided while being exposed to the liquid space 120 of the reactor.

The structure to which cyclododecene is supplied is not limited as long as cyclododecene or a mixed solution including cyclododecene may be supplied to the inner space of the reactor, and various means such as a method of introducing cyclododecene to the inside of the reactor without a separate supply member or a structure of supply with a separate supplying inlet in the inside of the reactor may be adopted. When there is the supplying inlet, the hydrogen gas may be supplied the gaseous space 110, the liquid space 120, or both of them in the structure, and there may be a supplying inlet in the inside of the reactor in which the hydrogen gas may be supplied to each space.

The number of openings (211 and 212) formed is not particularly limited, and for example, may be 1 to 10, and specifically 2 to 8, and the arrangement of the openings (211 and 212) is also not particularly limited. Furthermore, the size and the shape of the openings (211 and 212) is not largely limited as long as the hydrogen gas may be sufficiently supplied, and the openings may have various shapes such as round, oval, n-polygonal (n is a natural number of 3 or more), and irregular shapes, for example. However, this has been described as a specific example, and the present invention is not limited thereto, of course.

For the one end portion or the other end portion of the impeller shaft 210 mentioned in the present invention, the terms, a one end or the other end are only used for description and do not mean only ends such as a one end and the other end, and as the term is defined as a part, the terms are interpreted widely as including even a side surface of the impeller shaft 210, of course.

Figure 3:
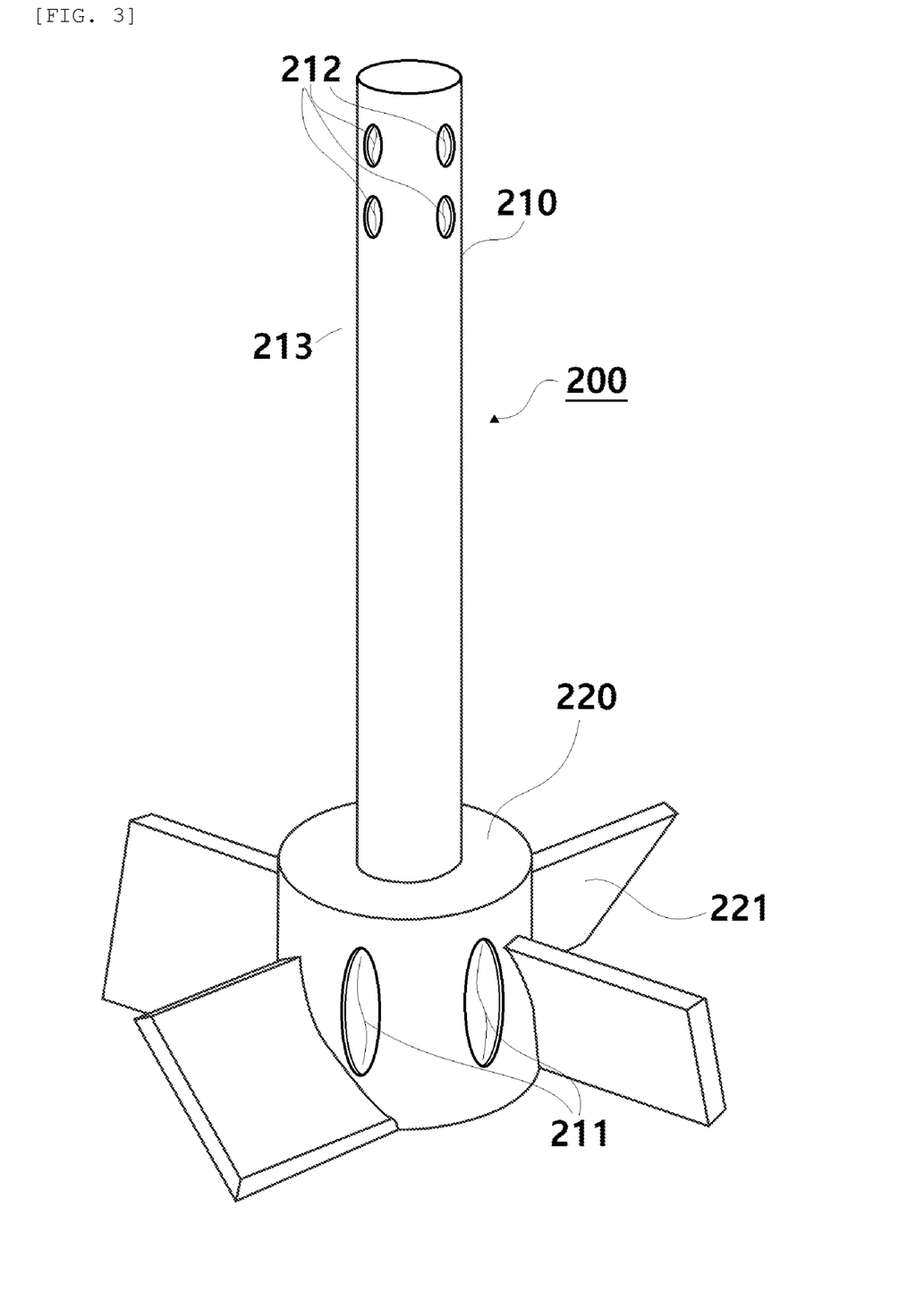

As described above, the opening 211 formed in the end portion of the impeller shaft 210 and the opening 212 formed in the other end portion of the impeller shaft 210 may be formed at various positions of the agitator, and for example, as shown in FIG. 2, each of the openings may be formed in a one end portion and the other end portion of the impeller shaft 210, and as shown in FIG. 3, may be formed in the side surface of the impeller shaft 210.

As a preferred example, the opening 211 formed in the one end portion of the impeller shaft 210 and the opening 212 formed in the other end portion of the impeller shaft 210 may be independently of each other positioned in the side surface of the impeller shaft 210, as shown in FIG. 3, so that each of the openings is more exposed to the liquid space 120 and the gaseous space 110. When the opening 211 formed in the one end portion of the impeller shaft 210 is positioned in the side surface of the impeller shaft 210, negative pressure formation of a hallow portion is more derived by force of a blade 211 to push out a liquid phase, and thus, the effects described above such as a decrease in a reaction time may be implemented better, which is thus preferred.

Other than that, the specific structure not mentioned of the gas induction hollow-type agitator 200, for example, a diameter of the hollow portion 213, a passage length of the hollow portion 213, a length of the shaft 210, a diameter of the shaft 210, a structure/form of the impeller 220, a combined structure of the shaft 210 and the impeller 220, an angle of the blade 221 formed in the impeller 220, a size of the blade 221, a shape of the blade 221, a specification/scale of the agitator 220, and the like may be appropriately adjusted without being limited, and thus, any known literature may be referenced.

In the synthesis method of cyclododecene according to the present invention, a stirring speed is an important factor for the conversion rate of a reactant and the selectivity of a required product. That is, in the hydrogenation, the stirring speed may be 400 to 3,000 rpm, preferably 1,600 rpm or less, specifically 600 to 1,600 rpm, and more preferably 800 to 1,600 rpm. In the synthesis method of cyclododec- following the partial hydrogenation reaction of cyclodode- catriene, when the stirring speed of the gas induction hollow-type agitator 200 is in a preferred range, the reaction time may be decreased to less than 5 hours, specifically 4.5 hours or less, and more specifically 3.5 hours or less, while the conversion rate and the selectivity are 98% or more, which is thus preferred. However, when a non-hollow-type common agitator, not the gas induction hollow-type agitator 200, is used, the reaction time is 5 hours or more which is long even in the above preferred stirring speed range.

In the synthesis method of cyclododecene according to the present invention, the reaction pressure may be also regarded as one of important factors influencing the conversion rate of the reactant and the selectivity of the required product. As a preferred example, in the hydrogenation, the reaction pressure may be 10 to 80 bar, preferably 10 to 50 bar, and more preferably 15 to 40 bar. When this is satisfied, the gas induction hollow-type agitator 200 rotates to apply a negative pressure to the inside of the hollow portion 213, so that an appropriate pressure difference between the outside of the agitator 200 and the inside of the hollow portion 213 may be more stably formed. Therefore, since stable and reproducible implementation is possible together with the effects described above, a decrease in the effects due to other variables in the process may be minimized, and the present invention may be more effectively applied to, in particular, massification and commercialization.

In the hydrogenation, the reaction temperature may be any temperature at which the reaction proceeds, and may be 100 to 200° C., in terms of process efficiency for the reaction time and the like. However, this is described as a preferred example, and the present invention is not interpreted as being necessarily limited thereto.

As the catalyst, both a homogeneous catalyst and a heterogeneous catalyst may be used, but a homogeneous catalyst may be preferred in terms of further improving the effects described above. As a preferred example, the homogeneous catalyst may include ruthenium chloride ($RuCl_3$), triphenylphosphine (TPP), formaldehyde, and the like. The formaldehyde may be used as it is, or formalin which is a commercial product including formaldehyde at a constant concentration may be used.

In the catalyst, triphenylphosphine may form a complex in ruthenium chloride to act as the catalyst of the partial hydrogenation reaction, and the reaction may be more activated in the presence of formaldehyde.

In the catalyst, a mole ratio between ruthenium chloride and triphenylphosphine may be only such that catalysis is performed so that cyclododecatriene is hydrogenated to be converted into cyclododecene, and may be 1:100 to 300, and a mole ratio between the triphenylphosphine and the formaldehyde may be 1:1 to 2. However, this is described as a preferred example, and the present invention is not interpreted as being necessarily limited thereto.

In the hydrogenation, the content of the catalyst used may be only such that hydrogenation is partially added to cyclododecatriene. As a specific example, 0.1 to 20 parts by weight, specifically 1 to 15 parts by weight, and more specifically 3 to 12 parts by weight of the catalyst may be used with respect to 100 parts by weight of cyclododecatriene. However, this is described as a preferred example, and the present invention is not interpreted as being necessarily limited thereto.

In an exemplary embodiment of the present invention, excellent reactivity may be maintained without use of an organic solvent, but if necessary, in the hydrogenation, an organic solvent such as acetic acid or ethanol may be further used. However, this is described as a preferred example, and since in the present invention, the conversion rate of the reactant and the selectivity of the required product are excellent even without use of the organic solvent, the present invention should not be interpreted as being limited thereto. When the organic solvent is used, 0.01 to 2 parts by weight of the solvent may be used with respect to 100 parts by weight of cyclododecatriene, but the present invention is not limited thereto.

The cyclododecene synthesized according to the present invention may be used in various uses, the use is not limited, and as an example, the cyclododecene may be used for laurolactam synthesis. Specifically, the cyclododecene synthesized according to the present invention may be used as an intermediate for laurolactam synthesis. When a product including cyclododecene prepared using the synthesis method or the synthesis device of cyclododecene according to the present invention is used as the intermediate of laurolactam synthesis, the selectivity of the targeted product is very high, and though the obtained product including a product even including unreacted materials, intermediates, by-products, and the like, obtained from the synthesis method or the synthesis device according to the present invention may be used as it is as the intermediate, the conversion rate and the selectivity in the final step of synthesizing laurolactam are significantly excellent.

A reactor for synthesizing cyclododecatriene according to the present invention is to subject cyclododecatriene to a partial hydrogenation reaction under a catalyst to synthesize cyclododecene, the reactor including: a reaction unit 100 having a reaction space formed inside; and a gas induction hollow-type agitator 200 provided in the reaction space, wherein the gas induction hollow-type agitator 200 includes an impeller shaft 210 having a hollow portion 213 inside to have openings formed in each of a one end portion and the other end portion; and an impeller 220 formed in the one end portion of the impeller shaft 210, in which the opening is formed to communicate with an outside of the agitator 200.

In the reactor for synthesizing cyclododecene according to the present invention, the reaction space may include a gaseous space 110 formed in the upper portion and having a hydrogen gas; and a liquid space 120 formed in the lower portion and having a mixture including cyclododecatriene and a homogeneous catalyst, and an opening 211 formed in a one end portion of the impeller shaft 210 where the impeller 220 is positioned may be positioned in the liquid space 120, and the opening 212 formed in the other end portion of the impeller shaft 210 may be positioned in the gaseous space 110.

As described above, the reactor for synthesizing cyclododecene according to the present invention may be used to synthesize cyclododecene by the method described above. Therefore, the reactor may further include a control unit which may adjust each variable such as a stirring speed, a reaction temperature, and a supply flow rate of a reactant, in the method described above. As described above, since the stirring speed and the pressure in the inner space of the reactor may be an important means for implementing the effects, it is preferred that the reactor further includes a control unit controlling the stirring speed of the gas induction hollow-type agitator 200 and the pressure of the reaction space. The specific means for controlling each variable is already known in the art, and thus, reference may be made to known literatures.

When synthesis is performed using the synthesis method and the synthesis device according to the present invention, the conversion rate of cyclododecatriene and the selectivity of cyclododecene may be independently of each other 98% or more. Here, the upper limit of the conversion rate and the selectivity is 100%.

Hereinafter, the present invention will be described in detail by the Examples, however, the Examples are for describing the present invention in more detail, and the scope of the present invention is not limited to the following Examples.

Example 1

A reactor provided inside with a gas induction hollow-type agitator (gas inducing impeller) of FIG. 2 was used to subject cyclododecatriene to a hydrogenation reaction under a homogeneous catalyst to synthesize cyclododecene.

Specifically, a homogeneous catalyst including 0.044 g of ruthenium chloride ($RuCl_3$), 11.13 g of triphenylphosphine, and 5.31 g of formalin (an aqueous formaldehyde solution having a concentration of 37 wt %) (mole ratio of ruthenium chloride:triphenylphosphine:formaldehyde=1:200:292), 220 g of cyclododecatriene, 0.5 g of acetic acid, and 20 g of ethanol were introduced to the reactor, and the reactor was engaged. Subsequently, the reactor was purged three times with 5 bar of a nitrogen gas ($N_2$), purged three times with a hydrogen gas ($H_2$), and supplied with the hydrogen gas ($H_2$) to 6 bar. The gas induction hollow-type agitator of the reactor was operated at a stirring speed of x rpm (see Table 1 below), and the internal temperature of the reactor was raised to 145° C. for about 40 minutes. After the temperature was reached, when consumption of the hydrogen gas ($H_2$) was sensed, the reactor was supplied with the hydrogen gas ($H_2$) to 20 bar and the internal temperature of the reactor was raised to 160° C. for about 10 minutes. The reaction proceeded for y hours (see Table 1 below) from the time when the hydrogen gas was supplied (reaction time: 160° C.), and in order to prevent a pressure decrease by the hydrogen gas ($H_2$) at this time, the hydrogen gas ($H_2$) was continuously supplied so that the pressure was maintained during the reaction. The reaction time was determined as the time when the conversion rate was about 98%.

The cyclododecatriene was hydrogenated by the means to synthesize cyclododecene, and the conversion rate of cyclododecatriene and the selectivity of cyclododecene depending on the stirring speed and the reaction time were measured by the same means, with only the stirring speed (x) and the reaction time (y) being different, respectively. The results therefor are shown in the following Table 1.

Example 2

The conversion rate of cyclododecatriene and the selectivity of cyclododecene depending on the use of an organic solvent (acetic acid, ethanol) and the used content thereof were measured by the same means as in Example 1, except that the use of acetic acid and ethanol, the used content thereof, and the reaction temperature were adjusted as shown in the following Table 3. The results therefor are shown in the following Table 3.

Example 3

The conversion rate of cyclododecatriene and the selectivity of cyclododecene depending on the reaction temperature and the mole ratio of the catalyst were measured by the same means as in Example 1, except that the reaction temperature, the mole ratio (composition ratio) of the catalyst, and the reaction time were adjusted as shown in Table 4 (stirring speed: 1,600 rpm).

Comparative Example 1

The conversion rate of cyclododecatriene and the selectivity of cyclododecene depending on the stirring speed and the reaction time were measured by the same means as in Example 1, except that a common non-hollow-type agitator was used instead of the gas induction hollow-type agitator. The results therefor are shown in the following Table 2.

Comparative Example 2

The conversion rate of cyclododecatriene and the selectivity of cyclododecene depending on the use of an organic solvent (acetic acid, ethanol) and the used content thereof were measured by the same means as in Example 2, except that a common non-hollow-type agitator was used instead of the gas induction hollow-type agitator. The results therefor are shown in the following Table 3.

Experimental Example 1

<Evaluation of Conversion Rate, Selectivity, and Reaction Time Depending on Stirring Speed>

TABLE 1

|  | Example 1 | | | | |
| --- | --- | --- | --- | --- | --- |
| Reaction pressure (bar) | 20 | | | | |
| Reaction temperature (° C.) | 160 | | | | |
| Type of agitator | Hollow type | | | | |
| Stirring speed (rpm) | 600 | 800 | 1,200 | 1,600 | 2,000 |
| Conversion rate (%) | 98.2 | 98.3 | 98.3 | 98.5 | 98.5 |
| Selectivity (%) | 98.5 | 98.4 | 98.5 | 98.3 | 98.4 |
| Reaction time (h) | 4.5 | 3.5 | 3.0 | 2.5 | 2.5 |

TABLE 2

|  | Comparative Example 1 | | | |
| --- | --- | --- | --- | --- |
| Reaction pressure (bar) | 20 | | | |
| Reaction temperature (° C.) | 160 | | | |
| Type of agitator | Non-hollow type | | | |
| Stirring speed (rpm) | 600 | 800 | 1,200 | 1,600 |
| Conversion rate (%) | 98.3 | 98.2 | 98.3 | 98.5 |
| Selectivity (%) | 98.3 | 98.4 | 98.4 | 98.2 |
| Reaction time (h) | 5.5 | 5.0 | 5.0 | 5.0 |

As shown in Tables 1 and 2 above, in Comparative Example 1 using a common non-hollow-type agitator, a reaction time to obtain the required conversion rate (about 98%) was 5 hours or more even in the case of increasing a stirring speed. However, in Example 1 using a gas induction hollow-type agitator, a reaction time to obtain the required conversion rate (about 98%) was 4.5 hours or less and decreased to 2.5 hours or less with an increasing stirring speed, and a high selectivity of 98% or more was obtained. In addition, when the stirring speed was more than 1,200 rpm, the reaction time to obtain the required conversion rate was not further decreased.

Experimental Example 2

TABLE 3

|  | Examples 1 and 2 | | Comparative Example 1 and 2 | |
| --- | --- | --- | --- | --- |
| Reaction pressure (bar) | 20 | | | |
| Reaction temperature (° C.) | 160 | | | |
| Stirring speed (rpm) | 1,600 | | | |
| Type of agitator | Hollow | | Non-hollow | |
| Content of acetic acid used (g) | — | 0.5 | 0.25 | 0.5 | 0.5 |
| Content of ethanol used (g) | — | 20 | 5 | 5 | 20 |
| Conversion rate (%) | 98.5 | 98.5 | 49.9 | 73.7 | 98.5 |
| Selectivity (%) | 98.3 | 98.4 | 99.0 | 98.7 | 98.2 |
| Reaction time (h) | 2.5 | 2.5 | 5 | 5 | 5 |

As shown in the above Table 3, in the Comparative Examples using a common non-hollow-type agitator, when the same reaction time (5 hours) was given, a change range in the conversion rate of cyclododecatriene was 49.9 to 98.5% which was a very wide range, depending on the content of an organic solvent used. However, in Example 1 using the gas induction hollow-type agitator, the reaction time at the conversion rate and the selectivity of about 98% was 2.5 hours which was very short even without an organic solvent, and a change in the conversion rate and the selectivity depending on the organic solvent was substantially not shown.

DETAILED DESCRIPTION OF MAIN ELEMENTS

100: reaction unit, 110: gaseous space,
120: liquid space, 200: agitator,
210: impeller shaft, 211: opening formed in a one end portion
212: opening formed in the other end portion, 213: hollow portion,
220: impeller, 221: blade,
CDT: cyclododecatriene, CDEN: cyclododecene

The invention claimed is:

1. A synthesis method of cyclododecene, the method comprising a hydrogenation process of subjecting cyclododecatriene to a partial hydrogenation reaction in the presence of a catalyst comprising a homogeneous catalyst comprising ruthenium chloride to synthesize cyclododecene,
  wherein in the hydrogenation process, cyclododecatriene and a hydrogen gas are reacted in a stirring tank reactor provided with a gas induction hollow-type agitator to synthesize cyclododecene,
  wherein in the hydrogenation process, a reaction pressure is 15 to 80 bar, and
  wherein the hydrogenation process is performed without use of a carboxylic acid and produces cyclododecene with a selectivity of 98% or more.

2. The synthesis method of cyclododecene of claim 1, wherein in the hydrogenation process, the partial hydrogenation reaction is carried out by stirring the gas induction hollow-type agitator, and the hydrogen gas is supplied to cyclododecatriene through a hollow portion of the gas induction hollow-type agitator.

3. The synthesis method of cyclododecene of claim 2, wherein the stirring tank reactor includes a reaction space formed inside, and the reaction space includes a gaseous space formed in an upper portion and having a hydrogen gas and a liquid space formed in a lower portion and having a mixture including cyclododecatriene and the catalyst.

4. The synthesis method of cyclododecene of claim 3, wherein the gas induction hollow-type agitator includes: an impeller shaft having a hollow portion inside to have openings formed in each of a one end portion and the other end portion; and an impeller formed in the one end portion of the impeller shaft, in which the openings formed in the one end portion are formed to communicate with an outside of the agitator, and in the hydrogenation process, the stirring is performed while the openings formed in the one end portion of the impeller shaft where the impeller is positioned are positioned in the liquid space, and the formed in the other end portion of the impeller shaft are positioned in the gaseous space.

5. The synthesis method of cyclododecene of claim 1, wherein in the hydrogenation process, a stirring speed is 400 to 3,000 rpm.

6. The synthesis method of cyclododecene of claim 1, wherein in the hydrogenation process, a reaction temperature is 100 to 200° C.

7. The synthesis method of cyclododecene of claim 1, wherein the homogeneous catalyst further comprises triphenylphosphine and formaldehyde.

8. The synthesis method of cyclododecene of claim 7, wherein a mole ratio of the ruthenium chloride and the triphenylphosphine is 1:100 to 300, and a mole ratio of the triphenylphosphine and the formaldehyde is 1:1 to 2.

9. The synthesis method of cyclododecene of claim 1, wherein the synthesized cyclododecene is used for laurolactam synthesis.

* * * * *